United States Patent [19]

Bennett, Jr.

[11] 4,258,761

[45] Mar. 31, 1981

[54] REHYDRATOR

[76] Inventor: John T. Bennett, Jr., 18025 Lafayette Dr., Olney, Md. 20832

[21] Appl. No.: 35,868

[22] Filed: May 3, 1979

[51] Int. Cl.[3] .............................................. B65B 3/12
[52] U.S. Cl. .................................. 141/242; 141/258; 73/423 R; 222/309; 277/135
[58] Field of Search ............... 141/234, 237, 250, 260, 141/258, 284, 392, 67, 81, 21, 25, 27, 26, 238, 242; 73/425.4 P, 425.6, 423 A, 423 R; 222/263, 309; 277/135

[56] References Cited

U.S. PATENT DOCUMENTS

| | | | |
|---|---|---|---|
| 1,155,023 | 9/1915 | Winchester | 141/237 |
| 1,927,092 | 9/1933 | Howard | 141/260 |
| 2,897,852 | 8/1959 | Douchet | 141/260 |
| 3,380,401 | 4/1968 | Faerber | 141/237 |
| 3,568,735 | 3/1971 | Lancaster | 141/234 |
| 3,982,438 | 9/1976 | Byrd | 141/238 |
| 4,047,438 | 9/1977 | Sekine | 141/238 |
| 4,106,911 | 8/1978 | Marcelli | 141/237 |
| 4,115,200 | 9/1978 | Anderson | 141/237 |
| 4,116,247 | 9/1978 | Zanasi | 141/392 |

Primary Examiner—Houston S. Bell, Jr.
Attorney, Agent, or Firm—Sughrue, Rothwell, Mion, Zinn and Macpeak

[57] ABSTRACT

The rehydrator is comprised of a first plate having a plurality of hollow tubes secured in through apertures and extending from one side of the plate perpendicular thereto. A plurality of rods are secured to a second plate disposed parallel to the first plate and extend through respective tubes in the first plate. The second plate is guided for movement toward and away from the first plate on a plurality of guide rods and springs are provided to normally bias the second plate away from the first plate. The rods slide loosely within the tubes and upon movement of the second plate downwardly into engagement with the first plate, the ends of the rods will extend beyond the tubes so that upon immersion of the ends of the rods and tubes into a solution, the withdrawal of the rods into the tubes will cause a predetermined amount of fluid to be drawn into the tube. Subsequent extension of the rods past the ends of the tubes will cause the liquid therein to be dispensed into appropriate receptacles aligned with each tube.

8 Claims, 7 Drawing Figures

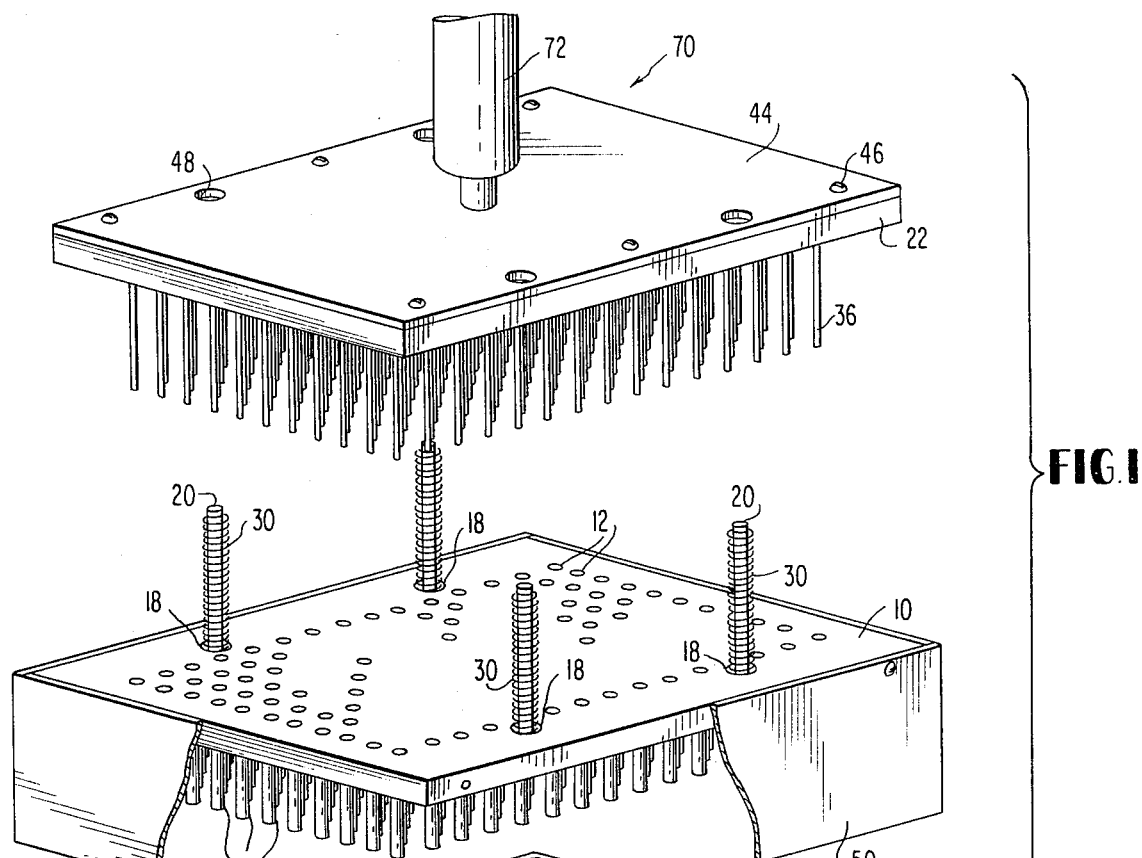
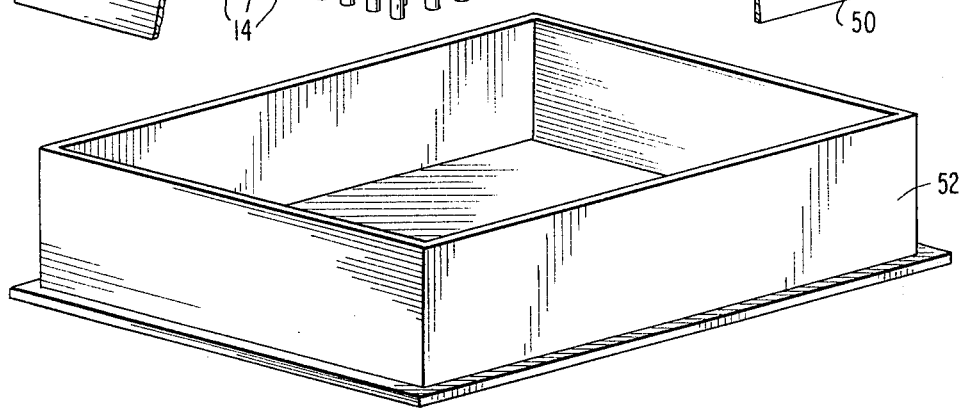
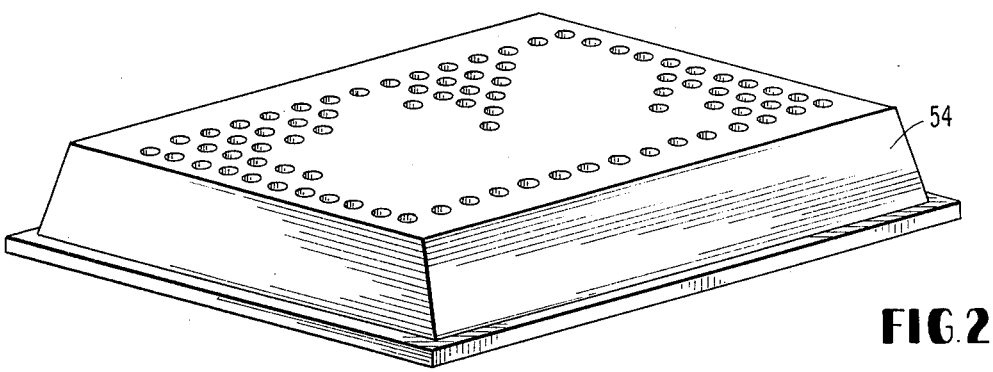
FIG.1
FIG.2

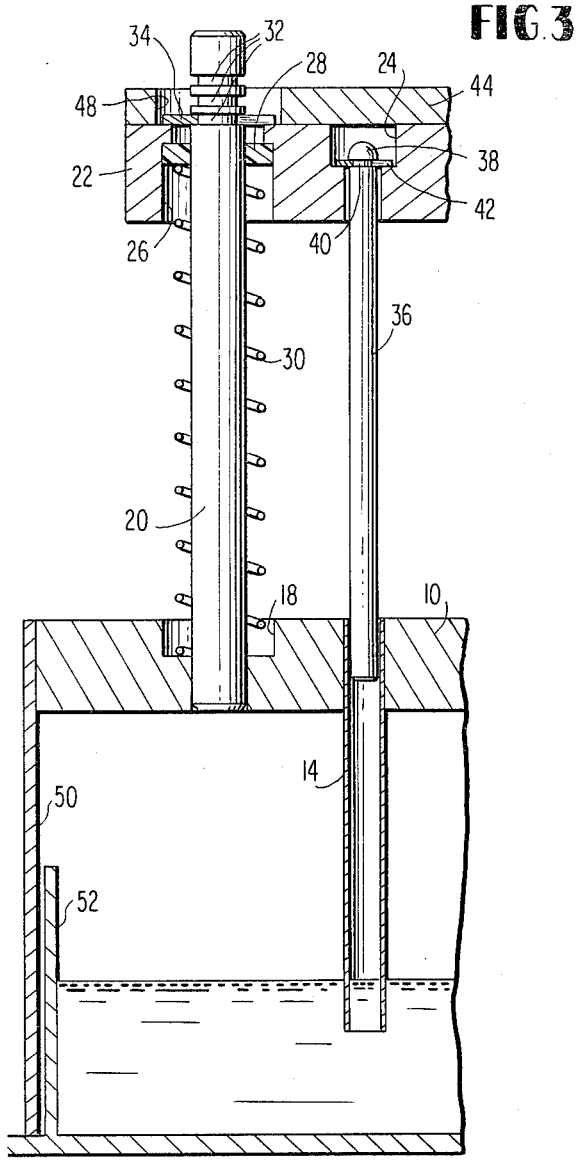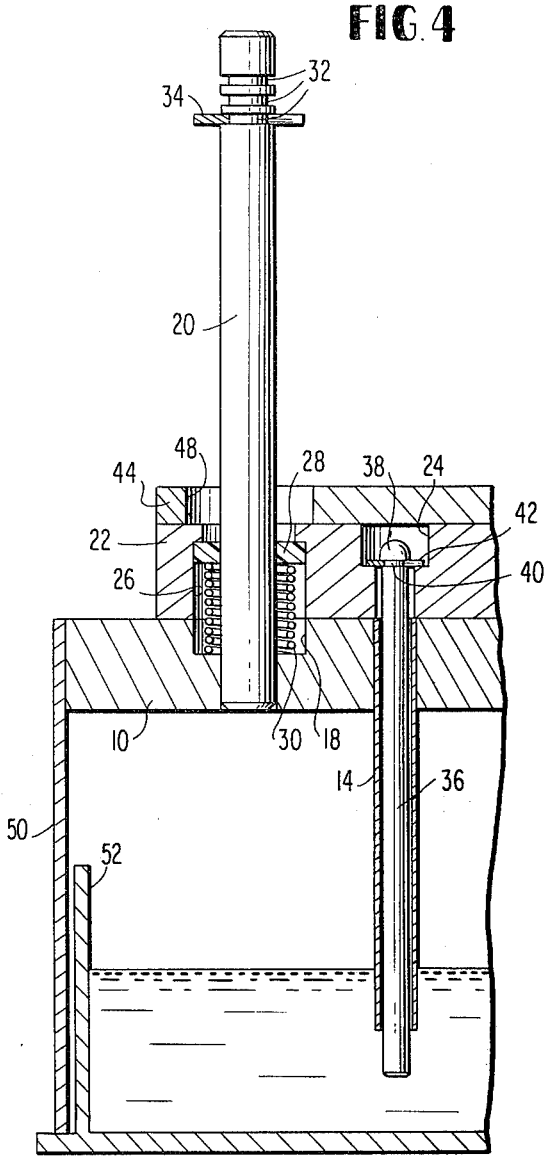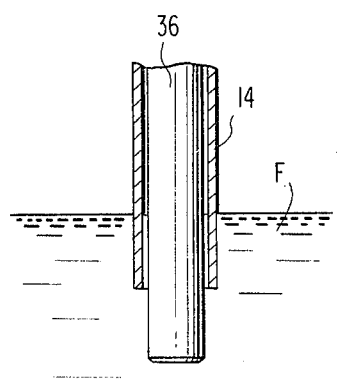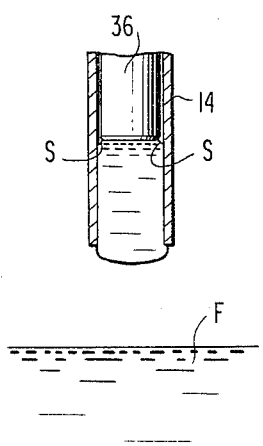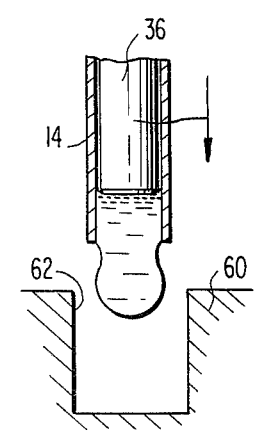

REHYDRATOR

BACKGROUND OF THE INVENTION

1. Field of the Invention

The present invention is directed to a rehydrator or microdispenser wherein a plurality of syringe type devices can simultaneously pickup predetermined quantities of fluid from a trough and dispense the same into a plurality of individual receptacles.

2. Prior Art

The patent to Sekine U.S. Pat. No. 4,047,438 is directed to a liquid quantitative dispensing apparatus comprised of a plurality of pipettes arranged in rows in a first plate member. A flexible sheet of rubber or the like having a plurality of cap-like projections is disposed on the plate with each cap-like projection being disposed over the open upper end of a pipette. A plurality of plungers on a second plate are guided for vertical movement into and out of engagement with the cap-like projections to control the air within the cap-like projections to withdraw fluid from a reservoir into the pipettes and to subsequently dispense the liquid into a plurality of wells which are moveable under the pipettes.

The patent to Byrd U.S. Pat. No. 3,982,438 is directed to a multiple sample pipetting apparatus which operates on the same principle as the Sekine patent with the exception that the positive air pressure is used to control deflection of a diaphragm to control the air within the individual pipettes which in turn will control the picking up and dispensing of fluid.

The patent to Marcelli U.S. Pat. No. 4,106,911 is directed to a device for dispensing a plurality of microdoses of a liquid. A plurality of syringes are mounted on a fixed support and the plungers are all secured to a plate which is mounted for vertical reciprocating movement by means of a motor operating through a screw and nut arrangement. A support is also mounted for vertical movement below the syringes for supporting various trays having either a reservoir or a plurality of recepticles. The plungers of each syringe are slidably mounted within the body and are provided with a ring of sealing material adjacent the end thereof to provide a slidable airtight connection between the plunger and the body of the syringe.

The patent to Lancaster U.S. Pat. No. 3,568,735 is directed to a laboratory dispensing apparatus wherein a common diaphragm overlies a plurality of pistons which are reciprocable within chambers formed in a plate. The pistons are provided with a rod which is slidably disposed in a barrel to control the pickup and dispensing of fluid.

The patent to Zanasi U.S. Pat. No. 4,116,247 is directed to a dosing device which is comprised of a tubular housing which is vertically moveable up and down. A hollow punch is secured to the lower end of the housing and a piston is slidably disposed within the hollow punch for reciprocating movement. The piston rod is secured at its upper end to an actuating rod by means of a magnetic connection. In operation, the hollow punch is inserted into a supply of powdered material all the way to the bottom of the container holding the powdered material. Depression of the piston will then compact the powdered material within the punch. The punch may then be withdrawn and upon further movement of the piston in the same direction, the plug of compacted powdered material will be ejected.

SUMMARY OF THE INVENTION

The present invention provides a new and improved rehydrator which is inexpensive in construction, easy to use and extremely accurate in operation.

The present invention is directed to a new and improved rehydrator comprised of a plurality of syringe-like devices having the barrel portions thereof secured to a first plate and the plungers thereof secured to a second plate. Due to the loose fitting sliding engagement of the plungers within the barrels, close tolerances need not be maintained in locating the barrels and plungers on their respective plates, thereby simplifying and expediting the construction of the rehydrator.

The present invention provides a new and improved rehydrator comprising a plurality of hollow barrels secured in apertures in a first plate and extending perpendicular thereto from the underside of the plate. A plurality of solid plungers are secured to a second plate disposed parallel to the first plate with the plungers slidably disposed within the hollow barrels. The second plate is guided for reciprocating movement toward and away from the first plate and spring means are provided for normally biasing the second plate away from the first plate to withdraw the plungers within the barrels. The plungers have sufficient length so that upon moving the second plate into contact with the first plate, the plungers will protrude beyond the ends of the barrels so that upon insertion of the ends of the barrels and plungers into a fluid reservoir with the plungers protruding beyond the ends of the barrels, the surface tension of the fluid will be broken and the ends of the barrels will be wetted. Upon withdrawal of the plungers into the barrels, a predetermined amount of fluid will be drawn up into the ends of the barrels. Upon positioning of the assembly over a tray having a plurality of individual wells or receptacles, the second plate can be moved toward the first plate thereby extending the ends of the plungers beyond the ends of the barrels to dispense the fluid contained in the barrels into respective wells or receptacles. Suitable frame means may be provided for spacing the first plate the correct distance above the fluid reservoir and the tray having the individual receptacles to ensure the proper operation of the rehydrator. Actuator means may also be secured to the frame means for moving the second plate toward and away from the first plate. The foregoing and other objects, features and advantages of the invention will be apparent from the following more particular description of a preferred embodiment of the invention as illustrated in the accompanying drawings.

BRIEF DESCRIPTION OF THE DRAWINGS

FIG. 1 is an exploded perspective view, partly broken away, showing the rehydrator according to the present invention.

FIG. 2 is a perspective view of a tray having a plurality of individual receptacles or wells therein.

FIG. 3 is a cross-sectional side elevation view showing one of the syringe-like elements and the guide means for guiding the second plate for movement relative to the first plate.

FIG. 4 is a view similar to FIG. 3 showing the second plate in engagement with the first plate.

FIG. 5 is a detailed showing, partly in section, of the barrel and plunger assembly immersed in a fluid prior to picking up a predetermined quantity of the fluid.

FIG. 6 is a view similar to FIG. 5 showing the barrel and plunger retracted out of the fluid with a predetermined amount of the fluid withdrawn into the end of the barrel by the plunger.

FIG. 7 is a view similar to FIG. 6 showing the fluid within the barrel about to be ejected therefrom by the downward movement of the plunger into a receptacle.

DETAILED DESCRIPTION OF THE INVENTION

The rehydrator as shown in FIG. 1 is comprised of a first plate 10 having a plurality of apertures 12 therethrough which are arranged in a plurality of rows. A plurality of hollow cylindrical barrels 14 are secured in each of the apertures 12 and protrude downwardly from the lower side of the plate 10. All of the barrels 14 are of equal length and may be secured in the apertures 20 by press fitting or other suitable means. Four stepped apertures 18 are also formed through the plate 10 and four guide posts 20 are secured in the smaller diameter portion of the apertures 18 and extend upwardly from the plate 10. A second plate 22 is disposed parallel to the plate 10 and is provided with a first plurality of stepped apertures 24 equal in number to and aligned with the apertures 12 in the first plate 10. Four additional stepped apertures 26 are also formed in the plate 22 in alignment with the stepped apertures 18 in the plate 10. A ring 28 of antifriction material such as teflon or the like is seated in the enlarged diameter portion of the aperture 26. A spring 30 surrounds the guide posts 20 and is seated at one end in the enlarged diameter portion of the aperture 18 and is seated against the bearing ring 28 in the enlarged diameter portion of the aperture 26. The upper end of the guide post 20 is provided with three grooves 32 adapted to receive a C clip 34 which will provide an upper limit stop for the plate 22 as it is biased upwardly by the spring 30. The spacing between the plates 10 and 22 can be adjusted by locating the C clip 34 in a different one of the grooves 32.

A plurality of plungers 36 are slidably mounted in the barrels 14 and extend into the stepped apertures 24 at their upper ends. The upper end of each plunger 36 is provided with a rounded end 38 and a groove 40 into which a C clip 42 is snapped. The C clip 42 is adapted to rest on the shoulder of the stepped aperture 24 so that upon upward movement of the plate 22 relative to the plate 10, the plungers 36 will be moved upwardly within the barrels 14. A cover plate 44 is secured to the upper surface of the plate 22 by means of a plurality of screws 46. The cover plate 44 covers the apertures 24 to prevent the removal of the plungers 36. However, a plurality of apertures 48 are provided in alignment with the stepped apertures 26 in the plate 22 to accommodate the upper ends of the guide post 20.

The guide post 20, the plungers 36 and the barrels 14 are so dimensioned relative to each other that the parts will be disposed in the manner shown in FIG. 3 when the plate 22 is biased away from the plate 10 to the full extent permitted by the adjustable clip 34. When the plate 22 is pressed downwardly into engagment with the plate 10 as shown in FIG. 4, the lower end of the plunger 36 will extend beyond the lower end of the barrel 14 and the spring 30 will be completely compressed within the recess defined by the two enlarged diameter portions of the apertures 18 and 26. The external diameter of the plungers 36 is somewhat smaller than the internal diameter of the barrel 14 so that substantial clearance is provided as best seen in FIGS. 5–7. As a result of this substantial clearance, the tolerances required in aligning the plungers with the barrels are fairly broad, thus, simplifying and expediting the manufacturing procedure.

The assembly as described above may be housed in a suitable frame work or housing depending upon the particular use to which the dispenser will be put. A simplified example of such a housing is constituted by the wall portions 50 which are secured to and depend downwardly from the edges of the plate 10. The distance to which the walls 50 extend below the undersurface of the plate 10 is greater than the distance the lower end of the plunger 36 extends below the undersurface of the plate 10 when disposed in the position as shown in FIG. 4. Thus, the lower edges of the walls 50 will properly space the lower end of the plunger 36 and accordingly, the lower end of the barrel 14 from the bottom of a fluid reservoir 52 by a predetermined amount. Thus, if the reservoir 52 is filled to a predetermined level, the lower end of the plunger 36 as well as the lower end of the barrel 14 will be disposed below the surface of the fluid within the reservoir. Since the plunger is extending beyond the end of the barrel below the surface of the fluid, the surface tension will be broken and the end surfaces of the plunger will be thoroughly wetted as shown in FIG. 4 and 5. The plunger is then withdrawn into the barrel 14 and due to the liquid seal S formed between the interior surface of the barrel and the bottom edge of the plunger, a predetermined amount of fluid will be drawn into the barrel and the barrel may then be withdrawn from the fluid F as shown in FIG. 6. A microtray 60 having a plurality of wells 62 formed therein corresponding to the number of barrel and plunger assemblies can then be located beneath the respective barrel and plunger assemblies as shown in FIG. 7. Upon depression of the plurality of plungers in the direction of the arrow in FIG. 7, the fluid held within the lower end of the barrel will be dispensed into its respective well 62. The plunger assembly 70 comprised of the plates 22 and 44 and the plurality of rods 36 can be reciprocated by means of a suitable actuator 72 as shown in FIG. 1. The actuator may be fludic, mechanical or electrical and it may be mounted in a suitable frame or housing secured to the plate 10 similar to the manner in which the actuator 11 of the Sekine U.S. Pat. No. 4,047,438 is mounted in the housing 8 secured to the plate 3.

The state-of-the-art in microtube tray methodology calls for drying the test reagents in the microtube tray 54 as opposed to freezing until ready for use. The advantages of the drying instead of freezing are an increased shelf-life and the elimination of the problem of thawing during transportation. However, the use of dried reagents presented a problem in reconstituting the reagents just prior to use since it was extremely difficult to accomplish this simultaneously, accurately and economically. The rehydrator according to the present invention picks up from the fluid reservoir 52 and dispenses a fixed amount, for example 100 $\mu$l of fluid into each well of a microtube tray 54. The rehydrator performs like a battery of syringes held in the exact configuration of the wells of the microtube tray. However, a battery of syringes would be very costly as well as time consuming in the sterilization and cleaning process as there might be up to 176 wells to be filled in a tray.

According to the present invention the plunger assembly can readily be disconnected from the barrel assembly and the parts easily and efficiently sterilized. The materials used should be stainless steel, aluminum or the like which are susceptible to being autoclaved.

The rehydrator according to the present invention is also much easier to assemble than a battery of syringes since the tolerances can be much greater and there is no need for airtight seals between the plungers and the barrels. Since the ends 38 of the plungers are rounded there will be substantially point contact with the cover 44 during downward movement of the plunger assembly to avoid any problems which might arise due to misalignment of one or more barrels.

The housing or frame constituted by the walls 50 could be a separate structure upon which the plate 10 would merely rest during the pickup and dispensing procedure so that the housing 50 would not have to be sterilized after each operation.

While the invention has been particularly shown and described with reference to a preferred embodiment thereof, it will be understood by those in the art that various changes in form and details may be made therein without departing from the spirit and scope of the invention.

What is claimed is:

1. A rehydrator comprising first plate means having at least one aperture extending therethrough, at least one barrel means secured in said aperture and extending downwardly perpendicular to said first plate means, said barrel means having an end remote from said first plate means adapted to be immersed in a liquid guide means secured to said first plate means and extending upwardly perpendicular thereto, second plate means guided on said guide means for reciprocating movement toward and away from said first plate means and at least one plunger means mounted for movement with said second plate means and extending into said barrel means for sliding movement therein, said plunger means having a loose fit within said barrel means and having a length such as to extend beyond said end of said barrel means when said second plate means is moved into engagement with said first plate means and said end of said barrel means is immersed in a liquid to wet the end of said plunger to form a liquid seal between said plunger and said barrel so that upon retraction of said plunger means a predetermined amount of liquid will be drawn upwardly within the end of said barrel means.

2. A rehydrator as set forth in claim 1, further comprising a plurality of apertures extending through said first plate means, a plurality of barrel means secured in said apertures and a plurality of plunger means mounted for movement with said second plate means.

3. A rehydrator as set forth in claim 1, further comprising adjustable limit stop means on said guide means for limiting movement of said second plate means away from said first plate means and spring means associated with said guide means for normally biasing said second plate means away from said first plate means.

4. A rehydrator as set forth in claim 1, further comprising housing means for supporting said first plate means in predetermined relationship to reservoir means and microtube tray means adapted to be disposed beneath said barrel means and plunger means.

5. A rehydrator as set forth in claim 1, further comprising actuator means for moving said second plate means towards said first plate means.

6. A rehydrator as set forth in claim 1, wherein said plunger means has a loose sliding fit within said barrel means.

7. A rehydrator as set forth in claim 6, wherein the upper end of each plunger means is rounded to accomodate misalignments.

8. A rehydrator comprising hollow elongated barrel means having an end adapted to be immersed in a liquid, plunger means having a loose sliding fit located within said barrel means and means for guiding said plunger means for reciprocating movement within said barrel means, said plunger means having a length sufficient to extend beyond said end of said barrel means in one extreme position of movement when said end is immersed in liquid to wet the end of said plunger to form a liquid seal between said plunger and said barrel so that upon retraction of said plunger means a predetermined amount of liquid will be drawn upwardly within the end of said barrel means.

* * * * *